US00PP14135P29

(12) United States Plant Patent
Watanabe et al.

(10) Patent No.: US PP14,135 P2
(45) Date of Patent: Sep. 16, 2003

(54) CALIBRACHOA PLANT NAMED 'KIRIFU BLUE'

(75) Inventors: Hitoshi Watanabe, Kashiwa (JP); Daigaku Takeshita, Utsunomiya (JP)

(73) Assignee: Kirin Brewery Company, Ltd., Tokyo (JP)

( * ) Notice: Subject to any disclaimer, the term of this patent is extended or adjusted under 35 U.S.C. 154(b) by 0 days.

(21) Appl. No.: 10/122,734

(22) Filed: Apr. 14, 2002

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Calibrachoa plant named 'Kirifu Blue' characterized by its spreading and prostrate plant habit; freely branching growth habit; short internodes giving a dense bushy appearance; small leaves; early and freely flowering habit; small pale violet-colored flowers with darker violet-colored throat; and good weather tolerance.

1 Drawing Sheet

BOTANICAL CLASSIFICATION/CULTIVAR DESIGNATION

*Calibrachoa pygmaea*×*Calibrachoa parviflora* cultivar Kirifu Blue.

BACKGROUND OF THE INVENTION

The present Invention relates to a new and distinct cultivar of Calibrachoa plant, botanically known as *Calibrachoa pygmaea*×*Calibrachoa parviflora,* and hereinafter referred to by the name 'Kirifu Blue'.

The new Calibrachoa is a product of a planned breeding program conducted by the Inventors in Tochigi, Japan. The objective of the breeding program is to create new Calibrachoa cultivars with small leaves and flowers.

The new Calibrachoa originated from a cross-pollination made by the Inventors in April, 1995, in Tochigi, Japan, of an unnamed proprietary selection of *Calibrachoa pygmaea,* not patented, as the female, or seed, parent with an unnamed proprietary selection of *Calibrachoa parviflora,* not patented, as the male, or pollen, parent. The new Calibrachoa was discovered and selected by the Inventors as a single flowering plant within the progeny of the stated cross-pollination grown in a controlled environment in Tochigi, Japan, in September, 1996.

Asexual reproduction of the new cultivar by terminal cuttings taken in a controlled environment in Saitama-ken, Japan, since March, 1997, has shown that the unique features of this new Calibrachoa are stable and reproduced true to type in successive generations.

SUMMARY OF THE INVENTION

Plants of the cultivar Kirifu Blue have not been observed under all possible environmental conditions. The phenotype may vary somewhat with variations in environment such as temperature and light intensity without, however, any variance in genotype.

The following traits have been repeatedly observed and are determined to be the unique characteristics of 'Kirifu Blue'. These characteristics in combination distinguish 'Kirifu Blue,' as a new and distinct cultivar of Calibrachoa:

1. Spreading and prostrate plant habit.
2. Freely branching growth habit.
3. Short internodes giving a dense bushy appearance.
4. Small leaves.
5. Early and freely flowering habit.
6. Small pale violet-colored flowers with darker violet colored throats.
7. Good weather tolerance.

Plants of the new Calibrachoa can be compared to plants of the female parent, an unnamed proprietary selection of *Calibrachoa pygmaea.* In side-by-side comparisons conducted by the Inventors in Tochigi, Japan, plants of the new Calibrachoa differed from plants of the female parent in the following characteristics:

1. Flowers of plants of the new Calibrachoa were smaller than flowers of plants of the female parent.
2. Flowers of plants of the new Calibrachoa were pale violet in color whereas flowers of plants of the female parent were white in color.
3. Flowers of plants of the new Calibrachoa produced very little pollen whereas flowers of plants of the female parent produced abundant pollen.

Plants of the new Calibrachoa can be compared to plants of the male parent, an unnamed proprietary selection of *Calibrachoa parviflora.* In side-by-side comparisons conducted by the Inventors in Tochigi, Japan, plants of the new Calibrachoa differed from plants of the male parent in the following characteristics:

1. Flowers of plants of the new Calibrachoa were smaller than flowers of plants of the male parent.
2. Flowers of plants of the new Calibrachoa were pale violet in color whereas flowers of plants of the male parent were purple in color.

Plants of the new Calibrachoa differ primarily from plants of the Calibrachoa cultivars Kirifu Red, disclosed in a U.S. Plant patent application Ser. No. 10/122,690 filed concurrently, Kirifu Compact Blue, disclosed in a U.S. Plant patent application Ser. No. 10/122,689 filed concurrently, and Kirifu Compact Red, disclosed in a U.S. Plant patent application Ser. No. 10/122,688 filed concurrently, primarily in flower coloration and plant size.

Plants of the new cultivar can be compared to plants of the cultivar Liricashower Pink, not patented. In side-by-side comparisons conducted by the Inventors in Tochigi, Japan, plants of the new Calibrachoa differed from plants of the cultivar Liricashower Pink in the following characteristics:

1. Plants of the new Calibrachoa were not as broad as plants of the cultivar Liricashower Pink.

2. Flowers of plants of the new Calibrachoa were smaller than flowers of plants of the cultivar Liricashower Pink.

3. Flowers of plants of the new Calibrachoa were pale violet in color whereas flowers of plants of the cultivar Liricashower Pink were red purple in color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa. The photograph comprises a side perspective view of a typical flowering plant of 'Kirifu Blue' that was about 14 weeks from planting a rooted young plant.

DETAILED BOTANICAL DESCRIPTION

In the following description, color references are made to The Royal Horticultural Society Colour Chart, 1995 Edition, except where general terms of ordinary dictionary significance are used. Plants with one plant per 15.25-cm containers were grown under conditions which closely approximate commercial production conditions during the winter in Santa Paula, Calif., in a polyethylene-covered greenhouse. Plants used for the following description were about seven weeks from planting rooted young plants. During the production of the plants, day temperatures were about 24 to 32° C., night temperatures were about 18 to 21° C., and light levels were about 4,000 to 6,000 footcandles.

Botanical classification: *Calibrachoa pygmaea*× *Calibrachoa parviflora cultivar Kirifu Blue.*

Parentage:

*Female, or seed, parent.*—Unnamed proprietary selection of *Calibrachoa pygmaea,* not patented.

*Male, or pollen, parent.*—Unnamed proprietary selection of *Calibrachoa parviflora,* not patented.

Propagation:

*Type cutting.*—Terminal vegetative cuttings.

*Time to initiate roots.*—Summer: About 5 days at 25° C. Winter: About 7 days at 20° C.

*Time to produce a rooted young plant.*—Summer: About 21 days at 25° C. Winter: About 28 days at 20° C.

*Root description.*—Fine, fibrous, and white in color.

*Rooting habit.*—Freely branching; dense.

Plant description:

*Form.*—Flowering plant with spreading and prostrate plant habit; low mounded; short internodes, dense and bushy appearance.

*Plant height* (*from soil level to top of plant plane*).—About 8 cm.

*Plant diameter* (*area of spread*).—About 45 cm.

*Branching habit.*—Freely basal branching, about 46 basal branches per plant; lateral branches develop at potentially every node; pinching is typically not required.

*Lateral branch description.*—Length: About 32 cm. Diameter: About 2 mm. Internode length: About 1 cm. Orientation: Upright to horizontal; decumbent. Texture: Pubescent; short, fine hairs. Strength: Strong, but flexible. Color: 146C.

*Foliage description.*—Arrangement: Alternate before flowering, after flowering, opposite; simple. Quantity per lateral branch: More than 50. Length: About 1.7 cm. Width: About 4.5 mm. Shape: Oblanceolate to narrowly elliptic. Apex: Obtuse to broadly acute. Base: Attenuate. Margin: Entire. Texture, upper and lower surface: Coarse; slightly glandular; minute pubescence. Fragrance: Spicy. Venation pattern: Pinnate. Color: Young and fully expanded foliage, upper surface: 137A; venation, 137B. Young and fully expanded foliage, lower surface: 137C; venation, 137C. Petiole length: About 2.5 mm. Petiole diameter: About 2 mm. Petiole color: 144A.

Flower description:

*Flower type and habit.*—Flowers face upright or outward; solitary and axillary; salverform. Freely flowering habit, about 30 flowers and flower buds per lateral stem. Flowers persistent. Flowers not fragrant.

*Natural flowering season.*—Spring until frost in the autumn; flowering continuous during this period.

*Time to flower.*—Early flowering; plants begin flowering about two to three weeks after planting.

*Flower longevity on the plant.*—About one week.

*Flower size.*—Diameter: About 1.7 cm. Height (depth): About 1.5 cm. Throat diameter: About 3 mm. Tube length: About 1 cm. Tube base: About 2 mm.

*Flower buds* (*showing color*).—Length: About 1 cm. Diameter: About 2 mm. Shape: Roughly oblong. Color: 90A.

*Corolla.*—Arrangement/appearance: Single whorl of five petals, fused into flared trumpet. Petal length from throat: About 7 mm. Petal width: About 8 mm. Petal shape: Roughly spatulate. Petal apex: Rounded; cuspidate. Petal margin: Entire. Petal texture: Smooth, glabrous; satiny. Color: Petal, when opening, upper surface: 87C. Petal, when opening, lower surface: 87A to 87B. Petal, opened flower, upper surface: 85A to 85B; color does not fade with subsequent development. Petal, opened flower, lower surface: 84A. Flower throat (inside): 90A. Flower tube (outside): 148D; fine longitudinal stripes, 147B.

*Sepals.*—Arrangement/appearance: Single whorl of five sepals fused at base; star-shaped. Length: About 9 mm. Width: About 1 mm. Shape: Narrow, strap-like. Apex: Rounded. Margin: Entire. Texture, upper and lower surfaces: Minute pubescence. Color: Young and fully expanded sepals, upper surface: 147A. Young and fully expanded sepals, lower surface: 147B.

*Peduncles.*—Length: About 4.5 mm. Width: Less than 1 mm. Strength: Strong. Angle: About 45° from stem. Texture: Pubescent. Color: 147C.

*Reproductive organs.*—Stamens: Quantity: Five per flower; adnate to floral tube. Anther shape: Round. Anther length: Less than 1 mm. Anther color: 4C. Pollen amount: Scarce. Pollen color: 4C. Pistils: Quantity: One per flower. Pistil length: About 7 mm. Stigma shape: Rounded; curved. Stigma color:

145B. Style length: About 5 mm. Style color: 145C. Ovary color: 145C.

*Seed/fruit.*—Seed nor fruit production has not been observed.

Disease/pest resistance: Plants of the new Calibrachoa have not been noted to be resistant to pathogens and pests common to Calibrachoa.

Weather/temperature tolerance: Plants of the new Calibrachoa are tolerant to rain and wind and have been observed to tolerate temperatures from 3 to 35° C.

It is claimed:

1. A new and distinct cultivar of Calibrachoa plant named 'Kirifu Blue', as illustrated and described.

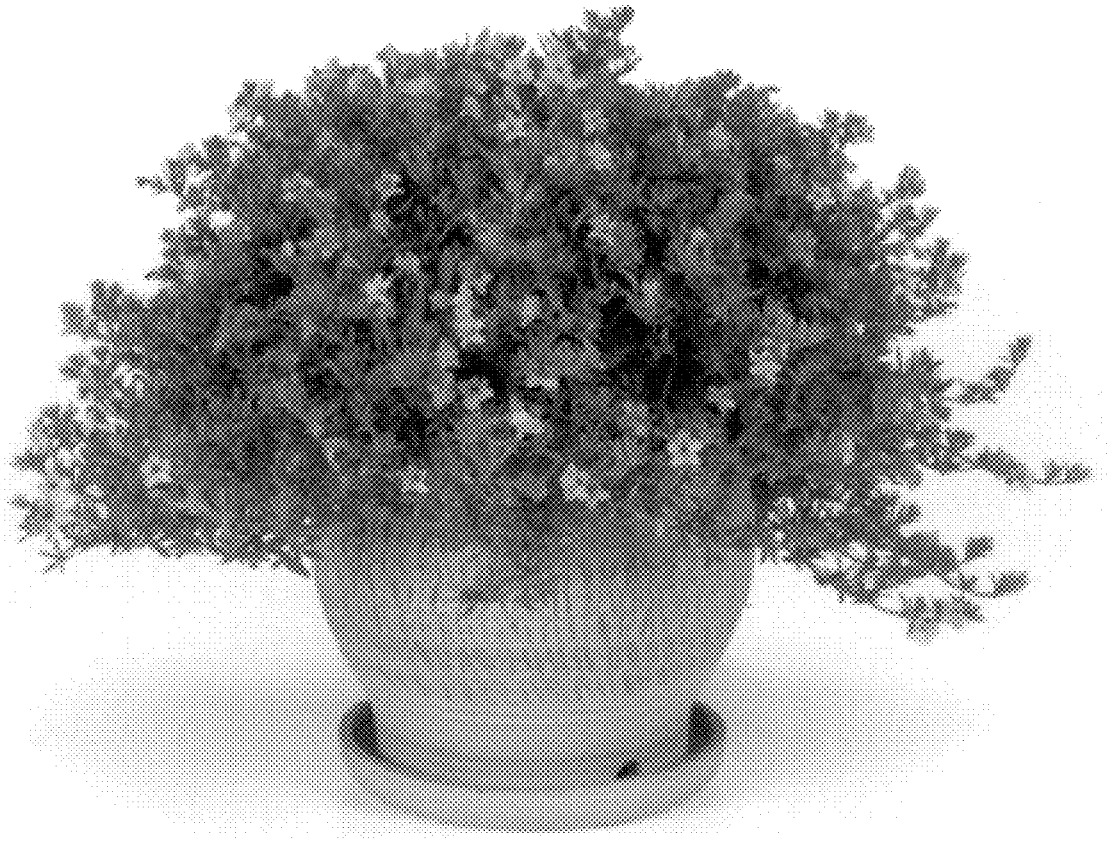

* * * * *